(12) United States Patent
Song et al.

(10) Patent No.: US 11,959,651 B2
(45) Date of Patent: Apr. 16, 2024

(54) METHOD FOR CLEANING AIR CONDITIONER AND AIR CONDITIONER

(71) Applicants: QINGDAO HAIER AIR CONDITIONER GENERAL CORP., LTD., Qingdao (CN); HAIER SMART HOME CO., LTD, Qingdao (CN)

(72) Inventors: Yujun Song, Qingdao (CN); Defang Guo, Qingdao (CN); Fei Wang, Qingdao (CN); Yang Li, Qingdao (CN); Hongjin Wu, Qingdao (CN); Xinyi Zhang, Qingdao (CN); Wenming Xu, Qingdao (CN)

(73) Assignees: QINGDAO HAIER AIR CONDITIONER GENERAL CORP.., LTD., Qingdao (CN); HAIER SMART HOME CO., LTD, Qingdao (CN)

( * ) Notice: Subject to any disclaimer, the term of this patent is extended or adjusted under 35 U.S.C. 154(b) by 89 days.

(21) Appl. No.: 17/801,484

(22) PCT Filed: Nov. 3, 2020

(86) PCT No.: PCT/CN2020/126306
§ 371 (c)(1),
(2) Date: Aug. 22, 2022

(87) PCT Pub. No.: WO2021/174891
PCT Pub. Date: Sep. 10, 2021

(65) Prior Publication Data
US 2022/0412592 A1   Dec. 29, 2022

(30) Foreign Application Priority Data

Mar. 3, 2020 (CN) .......................... 202010140876.1

(51) Int. Cl.
F24F 11/41 (2018.01)
F24F 8/20 (2021.01)

(52) U.S. Cl.
CPC ................ *F24F 11/41* (2018.01); *F24F 8/20* (2021.01); *A61L 2202/17* (2013.01); *F24F 2221/22* (2013.01)

(58) Field of Classification Search
CPC ......... A61L 2202/17; F24F 8/20; F24F 11/41; F24F 11/43; F24F 2221/22; F24F 2221/225
See application file for complete search history.

(56) References Cited

U.S. PATENT DOCUMENTS

2018/0259216 A1 * 9/2018 Zhang ...................... F24F 11/41

FOREIGN PATENT DOCUMENTS

| CN | 1476763 A | 2/2004 |
|----|-----------|--------|
| CN | 104764171 A | 7/2015 |

(Continued)

OTHER PUBLICATIONS

Extended European Search Report issued in counterpart European Patent Application No. 20923518.3, dated Jul. 21, 2023.

(Continued)

*Primary Examiner* — Jonathan Bradford
(74) *Attorney, Agent, or Firm* — Westbridge IP LLC

(57) ABSTRACT

A method for cleaning an air conditioner includes: in response to a cleaning instruction, controlling frosting on the surface of a target heat exchanger; after a frosting completion condition is met, controlling defrosting of the frost on the target heat exchanger; and after a defrosting completion condition is met, reducing the surface temperature of the target heat exchanger to a sterilization temperature, and carrying out quick cooling sterilization, wherein the temperature difference between the sterilization temperature and (Continued)

the defrosting temperature during defrosting meets a set temperature change sterilization condition. By a frosting-defrosting process, dirt such as dust on the heat exchanger may be effectively stripped and deep bacteria may be exposed, and then the quick cooling sterilization process may kill the bacteria by utilizing the sharp temperature change during switching from the defrosting process to the quick cooling process. Also disclosed is the air conditioner.

20 Claims, 2 Drawing Sheets

(56) References Cited

FOREIGN PATENT DOCUMENTS

| | | |
|---|---|---|
| CN | 104848738 A | 8/2015 |
| CN | 105135627 A | 12/2015 |
| CN | 105571078 A | 5/2016 |
| CN | 106152413 A | 11/2016 |
| CN | 106225176 A | 12/2016 |
| CN | 106642524 A | 5/2017 |
| CN | 107166670 A | 9/2017 |
| CN | 108489030 A | 9/2018 |
| CN | 108592294 A | 9/2018 |
| CN | 109489189 A | 3/2019 |
| CN | 110094840 A | 8/2019 |
| CN | 110207312 A | 9/2019 |
| CN | 110822631 A | 2/2020 |
| CN | 111536657 A | 8/2020 |
| JP | 2010014288 A | 1/2010 |
| JP | 2012052679 A | 3/2012 |
| JP | 2014045725 A | 3/2014 |
| JP | 2019039637 A | 3/2019 |

OTHER PUBLICATIONS

First Office Action issued in counterpart Chinese Patent Application No. 202010140876.1, dated Feb. 3, 2021.
International Search Report issued in corresponding PCT Application No. PCT/CN2020/126306, dated Jan. 28, 2021.
Second Office Action issued in counterpart Chinese Patent Application No. 202010140876.1, dated Jun. 17, 2021.
Written Opinion issued in corresponding PCT Application No. PCT/CN2020/126306, dated Jan. 28, 2021.
Refusal Decision issued in counterpart Japanese Patent Application No. 2022-544331, dated Jul. 6, 2023.

* cited by examiner

METHOD FOR CLEANING AIR CONDITIONER AND AIR CONDITIONER

CROSS-REFERENCE TO RELATED APPLICATIONS

The present application is the National Stage of International Application No. PCT/CN2020/126306, filed on Nov. 3, 2020, which claims priority to Chinese Patent Application No. 202010140876.1, filed on Mar. 3, 2020, the disclosure of which is incorporated in its entirety as reference herein.

TECHNICAL FIELD

The present application relates to the field of intelligent home appliance technologies, and in particular, to a method for cleaning an air conditioner and an air conditioner.

BACKGROUND

Currently, more and more users pay attention to the cleanliness and health of home environments, and as a common air apparatus for regulating the temperature and humidity of an indoor environment, an air conditioner has a level of cleanliness which can greatly influence the cleanliness of the indoor environment; from long-term use experience of the air conditioner, in the process of circularly conveying indoor air by the air conditioner, dust, impurities, or the like, in the indoor environment may enter the air conditioner with airflow, such that much dirt may be accumulated in the air conditioner after long-term use. In view of this situation, existing air conditioner manufacturers also develop and manufacture many air conditioner products with self-cleaning functions, such as an air conditioner with a heat-exchanger spray rinsing function, an air conditioner with a heat-exchanger steam washing function, or the like.

During realization of embodiments of the present disclosure, a related art is found to at least have the following problems:

the air conditioner is easy to accumulate much dirt in the using process, and when the air conditioner runs in a cooling mode in high-temperature weather in summer, much condensed water may be condensed on the surface of a heat exchanger, such that microorganisms, such as bacteria, mold, or the like, are quite easy to breed inside the air conditioner; the self-cleaning function of the existing air conditioner tends to be only aimed at dirt, such as dust, oil stains, or the like, and the existing air conditioner has poor cleaning effects on the breeding microorganisms.

SUMMARY

In order to provide a basic understanding of some aspects of the disclosed embodiments, a brief summary is given below. This summary is not intended to be an extensive review, nor to identify key/critical elements or to delineate the scope of protection of these embodiments, but rather serves as a prelude to the detailed description that follows.

Embodiments of the present disclosure provide a method for cleaning an air conditioner and an air conditioner, so as to solve the technical problem of a poor sterilization effect of the cleaning function of an air conditioner in the related art.

In some embodiments, the method includes:

in response to a cleaning instruction, controlling frosting on the surface of a target heat exchanger;

after a frosting completion condition is met, controlling defrosting of the frost on the target heat exchanger; and after a defrosting completion condition is met, reducing the surface temperature of the target heat exchanger to a sterilization temperature, and carrying out quick cooling sterilization, wherein the temperature difference between the sterilization temperature and the defrosting temperature during defrosting meets a set temperature change sterilization condition.

In some embodiments, an air conditioner includes: a processor and a memory storing program instructions, the processor being configured, when executing the program instructions, to perform the method for cleaning an air conditioner as shown in some embodiments above.

The method for cleaning an air conditioner and the air conditioner according to the embodiments of the present disclosure may have the following technical effects:

in the method for cleaning an air conditioner according to the embodiment of the present disclosure, frosting-defrosting and quick cooling sterilization processes may be carried out successively. By means of a frosting-defrosting process, dirt such as dust on the heat exchanger may be effectively stripped and deep bacteria may be exposed, and then the quick cooling sterilization process may kill the bacteria by utilizing the sharp temperature change during switching from the defrosting process to the quick cooling process; the method may effectively reduce microorganisms, such as bacteria, mold, or the like, on the heat exchanger, thereby improving the level of cleanliness inside the air conditioner.

The above general description and the following description are merely exemplary and explanatory and are not intended to limit the present application.

BRIEF DESCRIPTION OF THE DRAWINGS

One or more embodiments are exemplified by corresponding drawings. These exemplified descriptions and the drawings do not constitute a limitation on the embodiments. Elements with the same reference numerals in the drawings are denoted as similar elements. The accompanying drawings do not constitute a scale limitation, and in the drawings.

DETAILED DESCRIPTION OF THE EMBODIMENTS

In order to understand features and technical contents of the embodiments of the present disclosure in more details, implementations of the embodiments of the present disclosure will be described in detail hereunder in combination with the accompanying drawings. The accompanying drawings are only for reference and illustration, but not intended to limit the embodiments of the present disclosure. In the following technical description, for the convenience of explanation, a thorough understanding of the disclosed embodiments is provided through multiple details. However, without these details, one or more embodiments can still be implemented. In other cases, for simplification of the accompanying drawings, well-known structures and devices may be demonstrated in a simplified way.

The terminologies "first", "second", etc. in the specification, claims and aforesaid drawings of the embodiments of the present disclosure are used for distinguishing similar objects, but not necessarily for describing the specific order or sequence. It should be understood that the data so used may be interchanged as appropriate for the embodiments of the present disclosure described herein. Furthermore, the terms "including" and "having" and any variations thereof are intended to cover non-exclusive inclusion.

The term "a plurality of" means two or more unless otherwise stated.

In the embodiments of the present disclosure, the character "I" indicates an "or" relationship between associated objects. For example, A/B represents A or B.

The term "and/or" is an association relationship for describing objects and represents that three relationships may exist. For example, A and/or B represents the following three relationships: A, or B, or A and B.

Figure 1:
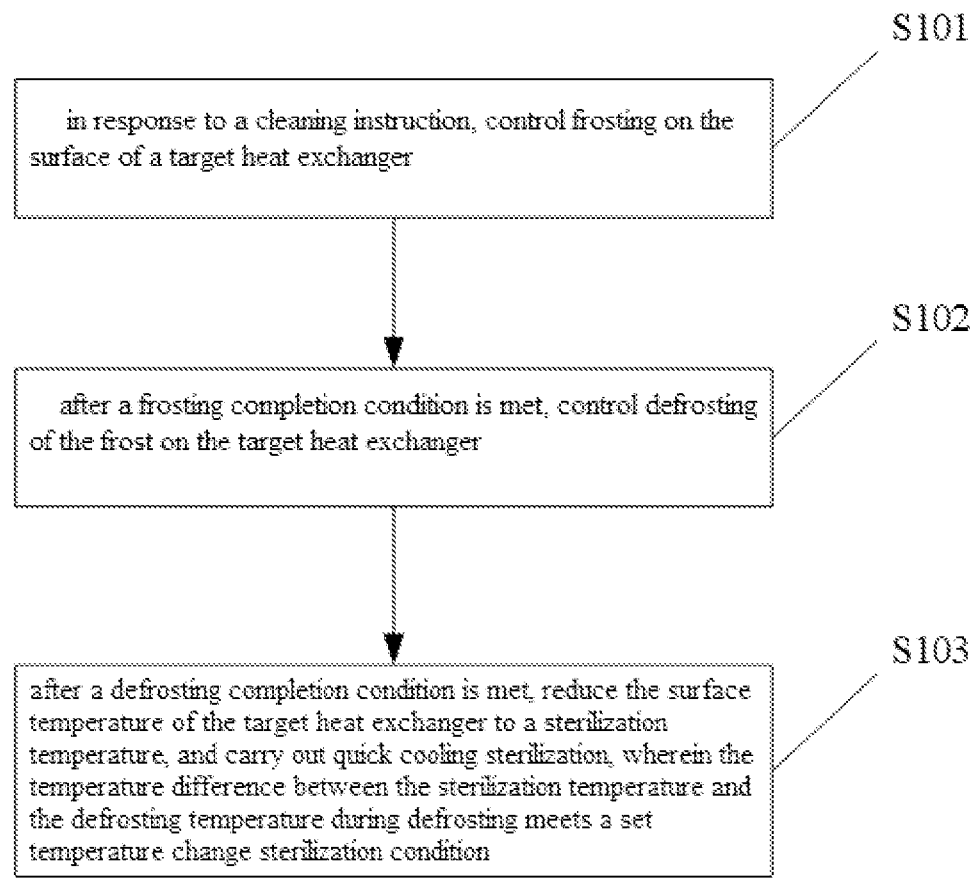
FIG. 1 is a schematic diagram of a method for cleaning an air conditioner according to an embodiment of the present disclosure.

FIG. 1 is a schematic diagram of a method for cleaning an air conditioner according to an embodiment of the present disclosure.

As shown in FIG. 1, the embodiment of the present disclosure provides a method for cleaning an air conditioner, which may be used to kill bacteria, mold, or the like, inside the air conditioner, and reduce the number of breeding microorganisms; in the present embodiment, the method includes:

S101: in response to a cleaning instruction, controlling frosting on the surface of a target heat exchanger.

In some optional embodiments, a cleaning option, such as "sterilization function" or "disinfection function", or the like, is added to a remote controller and a control panel of the air conditioner, and the cleaning option may be used to trigger the flow of the method for cleaning an air conditioner according to the present embodiment; thus, after a user selects the cleaning option, the air conditioner generates the related cleaning instruction and executes the cleaning instruction in response.

In some other optional embodiments, the air conditioner may also generate the related cleaning instruction by detection triggering, timing triggering, or the like; for example, the air conditioner additionally has a microorganism detection device which may be configured to detect the content of one or more specific types of microorganisms, and when the detected content of the microorganisms is higher than a set content threshold, it means that many microorganisms breed in the air conditioner, and the air conditioner generates the related cleaning instruction; or, the air conditioner has a timing module which may be configured to record accumulated running duration of the air conditioner, such as accumulated running duration of the cooling mode or the dehumidification mode; here, with the increase of the accumulated running duration of the cooling mode or the dehumidification mode of the air conditioner, more condensed water is condensed in the air conditioner, and more microorganisms breed in the humid environment, such that the air conditioner may be set to generate the related cleaning instruction when the accumulated running duration of the air conditioner exceeds a set duration threshold.

In still other optional embodiments, the air conditioner may also be triggered in linkage with an original cleaning function of the air conditioner; for example, after the original cleaning function is selected by the user, before or after execution of the cleaning flow defined by the original cleaning function, the cleaning instruction is generated and the flow of the cleaning method according to the present invention is executed; that is, after the user selects one original cleaning function, the air conditioner executes two different cleaning flows successively, and the cleanliness in the air conditioner is effectively guaranteed in a double cleaning mode.

For example, the original cleaning function of the air conditioner is a spray washing function that water is sprayed onto the heat exchanger of the air conditioner to clean the heat exchanger by means of running water flushing, and as an optional implementation, the flow of the cleaning method according to the present application is carried out before the spray washing function; that is, after the spray washing function is selected by the user, the flow of the cleaning method according to the present application is controlled to be executed to kill microorganisms, such as bacteria, or the like, and then, the spray washing function is executed, such that running water may wash away both dirt, such as dust, oil stains, or the like, and the killed microorganisms on the heat exchanger.

In the present embodiment, an indoor heat exchanger is mainly exemplified as the target heat exchanger, and when step S101 is executed, the air conditioner adjusts the flow direction of a refrigerant in a system to be consistent with the flow direction of the refrigerant in the cooling mode, such that the refrigerant input to the indoor heat exchanger is a low-temperature refrigerant, so as to reduce the temperature of the indoor heat exchanger using the heat absorption evaporation effect of the low-temperature refrigerant. In the present embodiment, the temperature of the indoor heat exchanger is reduced to the frosting critical temperature, such that when indoor air flows through the indoor heat exchanger, water vapor is condensed on the indoor heat exchanger, and the water vapor can strip the dirt, such as dust, oil stains, or the like, on the surface of the indoor heat exchanger in a gas state-liquid state-solid state conversion process, and therefore, the cleaning effect on pollutants with larger volumes may be improved, and meanwhile, the microorganisms in the deep layer of the dirt can be exposed, and thus can be killed more easily.

Optionally, the value range of the frosting critical temperature is lower than or equal to 0° C. In the present embodiment, the frosting critical temperature is 0° C.

S102: after a frosting completion condition is met, controlling defrosting of the frost on the target heat exchanger.

Optionally, the frosting completion condition includes:

$$t_{frosting} \geq t1_{frosting}$$

wherein $t_{frosting}$ is the duration of the frosting process in step S101, and $t1_{frosting}$ is a set frosting duration threshold. Optionally, the set frosting duration threshold ranges from 15 minutes to 17 minutes.

Here, the air conditioner has the timing module, and the timing module may be configured to record the duration of frosting on the surface of the target heat exchanger; after the air conditioner judges that the frosting completion condition is met according to the duration recorded by the timing module, the frost with an enough thickness is coagulated on the indoor heat exchanger, and at this point, a switching operation may be performed to defrost the indoor heat exchanger.

When the defrosting process of step S102 is executed, the air conditioner adjusts the flow direction of the refrigerant in the system to be consistent with the flow direction of the refrigerant in the heating mode, and at this point, the refrigerant input to the indoor heat exchanger is a high-temperature refrigerant, such that the indoor heat exchanger is heated by the high-temperature refrigerant, and the frost coagulated on the surface of the indoor heat exchanger is melted after absorbing heat, thereby realizing "defrosting". In the present embodiment, the temperature of the indoor heat exchanger is raised to a set defrosting temperature, and optionally, the defrosting temperature is 50° C., 55° C., or the like.

In the present embodiment, if the frosting completion condition is not met, the frosting process of step S101 is carried out continuously.

S103: after a defrosting completion condition is met, reducing the surface temperature of the target heat exchanger to a sterilization temperature, and carrying out quick cooling sterilization, wherein the temperature difference between the sterilization temperature and the defrosting temperature during defrosting meets a set temperature change sterilization condition.

Optionally, the defrosting completion condition includes:

$$t_{defrosting} \geq t2_{defrosting}$$

wherein $t_{defrosting}$ is the duration of the defrosting process in step S102, and $t2_{defrosting}$ is a set defrosting duration threshold. Optionally, the value range of the set defrosting duration threshold is longer than or equal to 30 minutes.

Here, the timing module of the air conditioner may be further configured to record the duration of defrosting of the target heat exchanger; after the air conditioner judges that the defrosting completion condition is met according to the duration recorded by the timing module, the frost coagulated on the indoor heat exchanger is melted completely.

In the present embodiment, if the defrosting completion condition is not met, the defrosting process of step S102 is carried out continuously.

Here, the air conditioner is provided with a temperature sensor at a coil pipe of the indoor heat exchanger, and the temperature sensor may be configured to detect the real-time temperature of the coil pipe of the indoor heat exchanger, such that whether the indoor heat exchanger reaches the frosting critical temperature and the defrosting temperature in steps S101 and S102 may be determined by comparison with temperature data detected by the temperature sensor; here, the timing module is reset after the frosting completion condition or the defrosting completion condition is determined to be met.

In some optional implementations, when the quick cooling sterilization flow in step S103 is executed, the air conditioner adjusts the flow direction of the refrigerant in the system to be consistent with the flow direction of the refrigerant in the cooling mode, such that a high-temperature refrigerant discharged by a compressor flows through an outdoor heat exchanger first, and then, a low-temperature refrigerant after throttling depressurization is input to the indoor heat exchanger, so as to absorb heat of the indoor heat exchanger using "cold energy" of the low-temperature refrigerant to reduce the temperature of the indoor heat exchanger again; the surface temperature of the indoor heat exchanger is reduced to the sterilization temperature to carry out quick cooling sterilization.

Optionally, the set temperature change sterilization condition includes:

$$T_{defrosting} - T_{sterilization} \geq T_{threshold}$$

wherein $T_{defrosting}$ is the defrosting temperature which is not lower than 56° C.; $T_{sterilization}$ is the sterilization temperature ranging from 0° C. to 5° C.; $T_{threshold}$ is not lower than 55° C.

Here, since the indoor heat exchanger is in a higher temperature state in the previous defrosting process and is switched to a lower temperature state in the later quick cooling sterilization process, the surface temperature of the indoor heat exchanger undergoes a large change of cold and heat, and an experiment proves that the sharp reduction process of this temperature can also effectively inactivate the microorganisms to achieve an enhanced sterilization effect.

For example, the defrosting temperature set in the defrosting process is 56° C., the corresponding sterilization temperature in the quick cooling sterilization process is 1° C., and the temperature difference between the two temperatures is 55° C., which meets the above-mentioned set temperature change sterilization condition; or the defrosting temperature is 59° C., the corresponding sterilization temperature in the quick cooling sterilization process is 2° C., and the temperature difference between the two temperatures is 57° C., which also meets the above-mentioned set temperature change sterilization condition.

In some optional embodiments, after step S103 is executed, if the quick cooling sterilization condition is met, quick cooling sterilization is controlled to be exited.

Optionally, the quick cooling sterilization condition includes:

$$t_{quick\ cooling} \geq t3_{quick\ cooling}$$

wherein $t_{quick\ cooling}$ is the duration of the quick cooling sterilization process, and $t3_{quick\ cooling}$ is a quick cooling sterilization duration threshold.

Optionally, the value range of $t3_{quick\ cooling}$ is longer than or equal to 10 minutes. In the present embodiment, $t3_{quick\ cooling}$ is 10 minutes. In the present embodiment, the aforementioned timing module may also be configured to record the duration of the quick cooling sterilization process after step S103.

In the present embodiment, if the quick cooling sterilization condition is not met, the quick cooling sterilization flow of step S103 is performed continuously.

In the method for cleaning an air conditioner according to the embodiment of the present disclosure, the frosting-defrosting and quick cooling sterilization processes may be carried out successively. By means of the frosting-defrosting process, dirt such as dust on the heat exchanger may be effectively stripped and deep bacteria may be exposed, and then the quick cooling sterilization process may kill the bacteria by utilizing the sharp temperature change during switching from the defrosting process to the quick cooling process; the method may effectively reduce microorganisms, such as bacteria, mold, or the like, on the heat exchanger, thereby improving the level of cleanliness in the air conditioner.

Figure 2:
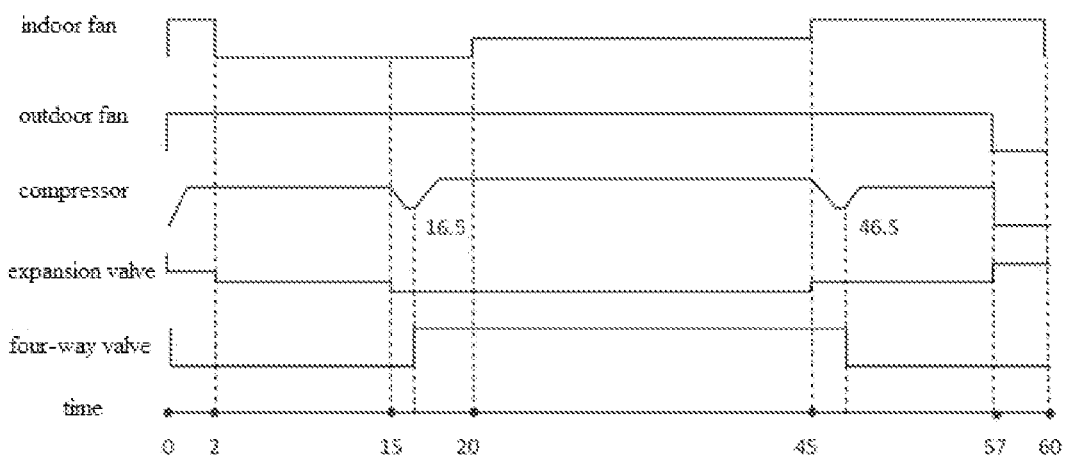
FIG. 2 is a schematic diagram of variations in parameters of various components in a cleaning process according to an embodiment of the present disclosure.

In the present embodiment, the sterilization effects of the frosting-defrosting process in S101 and S102 and the quick cooling sterilization process in S103 are mainly guaranteed by controlling working parameters of components, such as an indoor fan, an air deflector, an outdoor fan, a throttling device, the compressor and/or a four-way valve, or the like, and parameter control in each stage is exemplarily described below with reference to FIG. 2, in which the ordinate of FIG. 2 is a parameter amplitude change of each controlled component, and the abscissa is time.

(1) Frosting-Defrosting Process

Control steps of the indoor fan in the frosting-defrosting process are divided into three stages; in the first stage (condensation), the indoor fan is in a medium-wind rotating speed state (medium wind speed), and at this point, more indoor air flows through the indoor heat exchanger mainly through the operation of the indoor fan, such that more water vapor may be condensed into a liquid state from a gas state; in the second stage (frosting), the indoor fan is in a shutdown state, and at this point, the air conditioner inputs the low-temperature refrigerant to the indoor heat exchanger, and in order to cool the indoor heat exchanger as soon as possible to reduce the loss of cold energy to the indoor environment, the indoor fan is controlled to be in the shutdown state; in the third stage (defrosting), the indoor fan is in a low rotating speed state (low wind speed), and when sufficient frost is coagulated on the surface of the indoor heat exchanger after the two stages, defrosting is started, and the operation of the indoor fan in the low rotating speed state may accelerate the temperature rise inside an indoor unit, thereby increasing the defrosting speed.

Optionally, the three successive stages of the indoor fan may be set using fixed duration; for example, the total duration of the frosting-defrosting process is more than 45 minutes, the duration of the first stage is set to 2 minutes, the duration of the second stage is set to 13 minutes to 15 minutes, and the duration of the third stage is set to more than 30 minutes; thus, by recording the duration of each stage, the state of the indoor fan is controlled to be switched when a duration requirement is met.

In some optional embodiments, an air deflector of the indoor unit is in a closed state or a slightly opened state during the frosting-defrosting process, such that heat exchange between the indoor heat exchanger and the indoor environment during the frosting-defrosting process is reduced to guarantee the frosting efficiency in the frosting process and the defrosting efficiency in the defrosting process.

The frosting process includes a first coagulation parameter obtained according to the outdoor environment temperature, the first coagulation parameter including a second outdoor-fan rotating speed of the outdoor fan.

For control over the outdoor fan in the frosting process, the outdoor heat exchanger corresponding to the outdoor fan is in a heat release state, and the heat exchange temperature difference between the outdoor environment and the outdoor heat exchanger can influence the heat release efficiency of the outdoor heat exchanger, and thus influence the frosting effect on the indoor heat exchanger; here, the outdoor environment temperature and the outdoor fan are in a positive correlation relationship; that is, the higher the outdoor environment temperature is, the smaller the heat exchange temperature difference between the outdoor environment and the outdoor heat exchanger is, and the larger a heat exchange air volume required for guaranteeing the heat release effect is. Therefore, in the present embodiment, the rotating speed of the outdoor fan is adjusted according to the outdoor environment temperature, such that the heat release efficiency of the outdoor heat exchanger is enhanced, thus enhancing the frosting effect.

Optionally, a third association relationship between the outdoor environment temperature and the outdoor-fan rotating speed is preset in the air conditioner, and the third association relationship includes a one-to-one corresponding relationship between the outdoor environment temperature and the outdoor-fan rotating speed. Therefore, the outdoor-fan rotating speed corresponding to the current outdoor environment temperature can be obtained by searching the association relationship, and then, the outdoor fan is controlled to run with the outdoor-fan rotating speed as the second outdoor-fan rotating speed.

In still other optional embodiments, the frequency of the compressor can also affect the heat release efficiency of the outdoor heat exchanger. Here, the higher the running frequency of the compressor is, the larger the quantity of discharged refrigerants is, and the larger the quantity of the refrigerants flowing into the outdoor heat exchanger for heat exchange is. Therefore, in the present embodiment, the outdoor environment temperature and the frequency of the compressor are jointly used to determine the outdoor-fan rotating speed of the outdoor fan in the frosting stage, and table 1 shows an optional corresponding relationship between the outdoor environment temperature Tao and the frequency f of the compressor and the outdoor-fan rotating speed of the outdoor fan:

TABLE 1

| Outdoor environment temperature/frequency | $f < 51$ Hz | $51 \text{ Hz} \leq f \leq 80 \text{ Hz}$ | $f > 80$ Hz |
|---|---|---|---|
| Tao < 22° C. | 2 | 3 | 5 |
| 22° C. ≤ Tao ≤ 29° C. | 3 | 6 | 7 |
| Tao > 29° C. | 7 | 7 | 7 |

In the present embodiment, the rotating speeds of the outdoor fan are set into 7 settings with sequentially increased rotating speeds; table 1 shows the rotating speed settings of the outdoor fan corresponding to different combinations of the outdoor environment temperatures and frequencies, and in the present embodiment, control over the rotating speed of the outdoor fan in the frosting process may be determined by looking up the above table.

Similarly, a third rotating speed of the outdoor fan in the defrosting process may also be obtained according to the outdoor environment temperature. For control over the outdoor fan in the defrosting process, the outdoor heat exchanger corresponding to the outdoor fan is in a heat absorption state; here, the outdoor environment temperature and the outdoor fan are in a negative correlation relationship; that is, the lower the outdoor environment temperature is, the larger the heat exchange temperature difference between the outdoor environment and the outdoor heat exchanger is, and the larger a heat exchange air volume required for guaranteeing the heat absorption effect is. Therefore, in the present embodiment, the rotating speed of the outdoor fan is adjusted according to the outdoor environment temperature, such that the heat absorption efficiency of the outdoor heat exchanger is enhanced, thus improving the defrosting effect.

In still other optional embodiments, the frequency of the compressor can also affect the heat absorption efficiency of the outdoor heat exchanger, and therefore, in the present embodiment, the outdoor environment temperature and the frequency of the compressor are jointly used to determine the outdoor-fan rotating speed of the outdoor fan in the defrosting process, and table 2 shows an optional corresponding relationship between the outdoor environment temperature Tao and the frequency f of the compressor and the outdoor-fan rotating speed of the outdoor fan:

TABLE 2

| Outdoor environment temperature/frequency | f < 60 Hz | 60 Hz ≤ f ≤ 99 Hz | f > 99 Hz |
|---|---|---|---|
| Tao < 10° C. | 3 | 5 | 7 |
| 10 ≤ Tao ≤ 16° C. | 2 | 4 | 5 |
| Tao > 16° C. | 2 | 2 | 2 |

In the present embodiment, control over the rotating speed of the outdoor fan in the defrosting process may be determined by looking up the above table.

In the present embodiment, the frosting process further includes second coagulation parameters obtained according to the indoor environment temperature, the second coagulation parameters including a second frequency of the compressor and a second opening degree of the throttling device. Here, in the frosting process, the indoor heat exchanger is in a frosting state, and since the indoor unit is in the indoor environment, the frosting rate is influenced by the indoor environment temperature, and the higher the indoor environment temperature is, the greater the influence on frosting is. The frequency of the compressor can change the quantity of circulated refrigerants, and the opening degree of the throttling device can directly decide the temperature and the pressure of the refrigerant flowing into the indoor heat exchanger; in the present application, the frequency of the compressor and the opening degree of the throttling device are obtained according to the indoor environment temperature, such that the adjusted refrigerant can meet the demand of frosting the indoor heat exchanger, so as to reduce the influence of the indoor environment temperature on the frosting process.

Optionally, a fourth association relationship is preset in the air conditioner, and the association relationship includes a corresponding relationship between the indoor environment temperature and the frequency. In the association relationship, the indoor environment temperature and the frequency of the compressor are in a positive correlation relationship; that is, the higher the indoor environment temperature is, the higher the running frequency of the compressor is, and the larger the quantity of the low-temperature refrigerants input to the indoor heat exchanger is, such that a higher frosting effect can be achieved under a higher indoor environment condition.

Exemplarily, table 3 shows an optional corresponding relationship between the indoor environment temperature Tp and the frequency f of the compressor and the opening degree of the throttling device in the frosting process:

TABLE 3

| Indoor environment temperature | Tp ≥ 22° C. | Tp < 22° C. |
|---|---|---|
| Frequency | 90 Hz | 85 Hz |
| Opening degree | 220 | 230 |

In the present embodiment, control over the compressor and the throttling device in the frosting process may be determined by looking up the above table.

In some optional embodiments, in the defrosting process, both a third outdoor-fan rotating speed of the outdoor fan and a first opening degree of the throttling device may be obtained according to the outdoor environment temperature. Here, in the defrosting process, the refrigerant flows into the outdoor heat exchanger from the indoor heat exchanger, and in order to guarantee the defrosting effect in the defrosting process, the refrigerant flowing into the outdoor heat exchanger is required to be capable of absorbing more heat from the external environment, and therefore, in the present embodiment, the opening degree of the throttling device is adjusted to adapt to the heat exchange requirement under the current outdoor environment temperature condition.

In the present embodiment, the third outdoor-fan rotating speed of the outdoor fan and the first opening degree of the throttling device are defined as first defrosting parameters of the defrosting process. Here, a fifth association relationship is preset in the air conditioner, and the association relationship includes a corresponding relationship between the outdoor environment temperature and the outdoor-fan rotating speed or the opening degree.

Exemplarily, table 4 shows an optional corresponding relationship between the outdoor environment temperature Tao and the opening degree of the throttling device in the defrosting process:

TABLE 4

| Outdoor environment temperature | Tao ≥ 16° C. | 5° C. ≤ Tao < 16° C. | Tao < 5° C. |
|---|---|---|---|
| Opening degree | 220 | 240 | 260 |

Therefore, in the present embodiment, control over the opening degree of the throttling device in the defrosting process may be determined by looking up the above table.

(2) Quick Cooling Sterilization Process

The indoor fan runs at a rotating speed higher than that in the defrosting process in the quick cooling sterilization stage, such as a medium rotating speed, a high rotating speed, or the like; in the quick cooling sterilization stage, the refrigerant flows in a flow direction consistent with the flow direction in the cooling mode, the refrigerant input to the indoor heat exchanger is a low-temperature refrigerant, and since the entire interior of the indoor unit is in a higher temperature state after the previous defrosting process, in order to reduce the temperature of the indoor heat exchanger in a short time to achieve an effect of a sharp change of the temperature of the indoor heat exchanger, in the present application, the rotating speed of the indoor fan is increased to accelerate the heat exchange speed between internal hot air of the indoor unit and the low-temperature refrigerant, and meanwhile accelerate discharge of the hot air to the indoor environment, thus reducing the temperature of the indoor heat exchanger below the sterilization temperature.

In some embodiments not shown in the drawings, control over the rotating speed of the indoor fan in the quick cooling sterilization stage may also be determined according to the indoor coil pipe temperature.

Exemplarily, when the air conditioner starts to perform the quick cooling sterilization stage of step S103, the temperature of the coil pipe of the indoor heat exchanger is detected by a real-time temperature sensor, the indoor fan is controlled to be in the medium rotating speed state before the temperature of the coil pipe is decreased to the sterilization temperature, and the indoor fan is switched to the low rotating speed state or the shutdown state after the temperature of the coil pipe is decreased to the sterilization temperature. This control mode may improve quick cooling of the indoor heat exchanger in the quick cooling sterilization stage, thus improving and enhancing the sterilization effect.

In some optional embodiments, in the quick cooling sterilization stage, the air deflector of the indoor unit is in the slightly opened state, such that the discharge of the hot air of the indoor unit is accelerated to improve quick cooling. Meanwhile, according to the current cooling or heating working condition, the opening angle of the air deflector of the indoor unit may be further adjusted; for example, under the heating working condition, the air deflector of the indoor unit may be controlled to be opened by a slightly larger angle, such that more hot air can be discharged into the indoor environment, thus increasing the utilization rate of waste heat in the defrosting process; under the cooling working condition, the air deflector of the indoor unit is controlled to supply air upwards to avoid the cold air directly blowing the user, thus improving use experience of the user.

The quick cooling sterilization stage includes first quick cooling sterilization parameters obtained according to the outdoor environment temperature, the first quick cooling sterilization parameters including a first outdoor-fan rotating speed of the outdoor fan and a first frequency of the compressor.

For control over the outdoor fan in the quick cooling sterilization stage, the outdoor heat exchanger corresponding to the outdoor fan is in a heat release state, and the heat exchange temperature difference between the outdoor environment and the outdoor heat exchanger can influence the heat release efficiency of the outdoor heat exchanger, and thus influence the quick cooling effect on the indoor heat exchanger; here, the outdoor environment temperature and the outdoor fan are in a positive correlation relationship; that is, the higher the outdoor environment temperature is, the smaller the heat exchange temperature difference between the outdoor environment and the outdoor heat exchanger is, and the larger a heat exchange air volume required for guaranteeing the heat release effect is. Therefore, in the present embodiment, the rotating speed of the outdoor fan is adjusted according to the outdoor environment temperature, such that the heat dissipation efficiency of the outdoor heat exchanger is enhanced, thus improving the quick cooling sterilization effect.

Optionally, a first association relationship between the outdoor environment temperature and the outdoor-fan rotating speed is preset in the air conditioner, and the first association relationship includes a one-to-one corresponding relationship between the outdoor environment temperature and the outdoor-fan rotating speed. Therefore, the outdoor-fan rotating speed corresponding to the current outdoor environment temperature can be obtained by searching the association relationship, and then, the outdoor fan is controlled to run with the outdoor-fan rotating speed as the first outdoor-fan rotating speed.

In still other optional embodiments, the frequency of the compressor can also affect the heat release efficiency of the outdoor heat exchanger. Here, the higher the running frequency of the compressor is, the larger the quantity of discharged refrigerants is, and the larger the quantity of the refrigerants flowing into the outdoor heat exchanger for heat exchange is. Therefore, in the present embodiment, the outdoor environment temperature and the frequency of the compressor are jointly used to determine the outdoor-fan rotating speed of the outdoor fan in the quick cooling sterilization stage, and table 5 shows an optional corresponding relationship between the outdoor environment temperature Tao and the frequency f of the compressor and the outdoor-fan rotating speed of the outdoor fan:

TABLE 5

| Outdoor environment temperature/frequency | f < 51 Hz | 51 Hz ≤ f ≤ 80 Hz | f > 80 Hz |
|---|---|---|---|
| Tao < 22° C. | 2 | 3 | 5 |
| 22° C. ≤ Tao ≤ 29° C. | 3 | 6 | 7 |
| Tao > 29° C. | 7 | 7 | 7 |

In the present embodiment, the setting of the rotating speed settings of the outdoor fan is the same as that in the previous embodiment, and in the present embodiment, control over the rotating speed of the outdoor fan in the quick cooling sterilization stage may be determined by looking up the above table.

In some optional embodiments, the quick cooling sterilization stage has one key of lowering the temperature of the indoor heat exchanger below the sterilization temperature in a short time and maintaining the temperature; here, in the quick cooling sterilization stage, since the high-temperature refrigerant discharged by the compressor first flows to the outdoor heat exchanger, the outdoor environment temperature can influence the heat dissipation efficiency of the refrigerant in the outdoor heat exchanger and the outdoor environment, and thus influence the temperature of the refrigerant flowing into the indoor heat exchanger; then, in the present application, the frequency of the compressor is obtained according to the outdoor environment temperature, such that the adjusted frequency of the compressor can meet the requirement of quickly cooling the indoor heat exchanger to the sterilization temperature.

Optionally, the first association relationship further includes a one-to-one corresponding relationship between the outdoor environment temperature and the frequency of the compressor, such that the frequency of the compressor corresponding to the current outdoor environment temperature can be obtained by searching the association relationship.

For example, when the outdoor environment temperature is higher than a first outdoor environment temperature threshold, the compressor is controlled to run at a first frequency with a larger value, so as to increase the temperature and the quantity of the discharged refrigerant and improve the heat exchange efficiency of the refrigerant in the outdoor heat exchanger and the external environment; when the outdoor environment temperature is lower than the first outdoor environment temperature threshold, the heat exchange efficiency of the refrigerant and the outdoor environment is higher, and the compressor is controlled to run at a second frequency with a value less than that of the first frequency, thus effectively reducing the power consumption of the compressor in the quick cooling sterilization stage.

In some optional embodiments, the quick cooling sterilization stage further includes a second quick cooling sterilization parameter obtained according to the indoor environment temperature, the second quick cooling sterilization parameter including the first opening degree of the throttling device. In the present embodiment, the indoor fan in the quick cooling sterilization stage runs at a medium rotating speed, such that the indoor environment temperature influences the temperature of the indoor heat exchanger to a certain extent, and therefore, in order to guarantee the quick cooling sterilization effect, the opening degree of the throttling device is adjusted according to different temperature conditions of the indoor environment in the present embodiment, so as to change the temperature and pressure of the low-temperature refrigerant flowing into the indoor heat exchanger, thereby reducing the adverse influence of the indoor environment temperature on the quick cooling sterilization effect.

Optionally, a second association relationship is preset in the air conditioner, and the preset second association relationship includes a corresponding relationship between the indoor environment temperature and the opening degree. Table 6 shows the corresponding relationship between the indoor environment temperature Tp and the opening degree of the throttling device in an optional embodiment.

TABLE 6

| Indoor environment temperature | Tp ≥ 22° C. | Tp < 22° C. |
|---|---|---|
| Opening degree | 340 | 350 |

Therefore, in the present embodiment, control over the opening degree of the throttling device in the quick cooling sterilization stage may be determined by looking up the above table.

In some optional embodiments, when the operation of step S101 is performed, an electric auxiliary heating device may be further controlled to be activated for auxiliary heating, so as to accelerate the temperature rise inside the indoor unit using the electric auxiliary heating device, thereby shortening duration required by the indoor heat exchanger reaching a first sterilization temperature.

In some optional embodiments, after a high-temperature sterilization condition is met and before quick cooling sterilization is performed, since the flow direction of the refrigerant is required to be switched from the heating flow direction to the cooling flow direction, in order to guarantee the stability of the internal system of the air conditioner in the switching process, a pressure stabilizing operation is controlled to be performed in the present application, and the pressure stabilizing operation includes: opening the throttling device at the maximum opening degree, and reducing the frequency of the compressor; after the duration of the pressure stabilizing operation is determined to be longer than or equal to a set pressure stabilizing duration, quick cooling sterilization may be performed.

Optionally, the set pressure stabilizing duration is set to 1 minute to 2 minutes.

In some optional embodiments, the method for cleaning an air conditioner according to the present application further includes: controlling an ultraviolet sterilization device to be activated when the surface temperature of the target heat exchanger is heated to the first sterilization temperature. The ultraviolet sterilization device may utilize ultraviolet light to kill microorganisms inside the indoor unit, thereby improving the overall sterilization effect.

Figure 3:
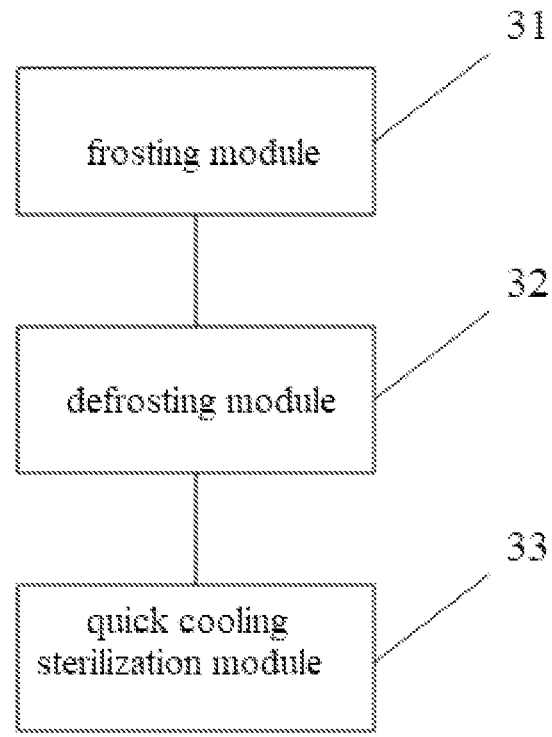
FIG. 3 is a schematic diagram of a device for cleaning an air conditioner according to an embodiment of the present disclosure.

As shown in FIG. 3, an embodiment of the present disclosure provides a device for cleaning an air conditioner, including a frosting module 31, a defrosting module 32, and a quick cooling sterilization module 33. The frosting module 31 is configured to, in response to a cleaning instruction, control frosting on the surface of a target heat exchanger; the defrosting module 32 is configured to, after a frosting completion condition is met, control defrosting of the frost on the target heat exchanger; and the quick cooling sterilization module 33 is configured to, after a defrosting completion condition is met, reduce the surface temperature of the target heat exchanger to a sterilization temperature, and carry out quick cooling sterilization, wherein the temperature difference between the sterilization temperature and the defrosting temperature during defrosting meets a set temperature change sterilization condition.

The device for cleaning an air conditioner according to the embodiment of the present disclosure is beneficial to reduction of microorganisms, such as bacteria, mold, or the like, on the heat exchanger, thereby improving the level of cleanliness inside the air conditioner.

Figure 4:
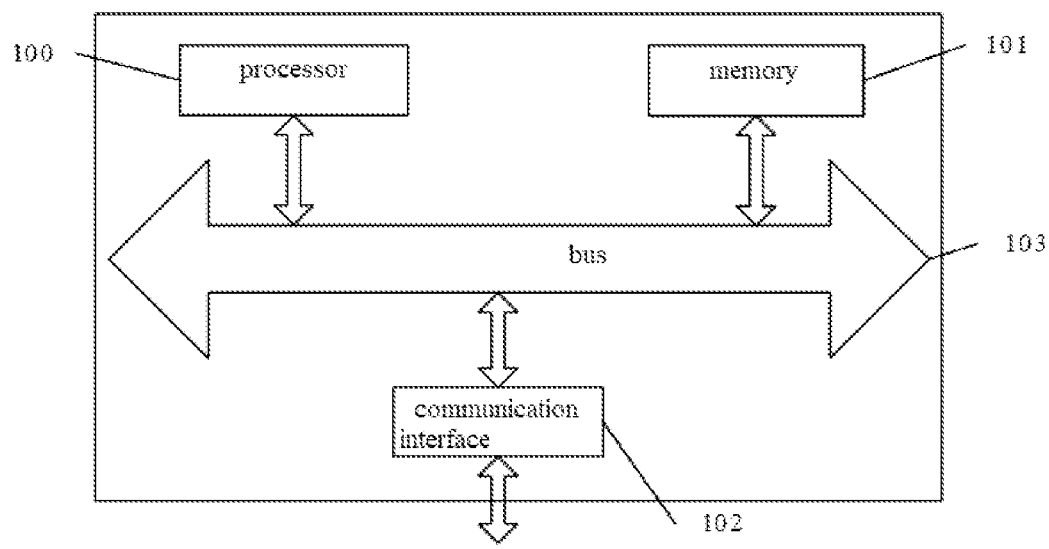
FIG. 4 is a schematic diagram of another device for cleaning an air conditioner according to an embodiment of the present disclosure.

As shown in FIG. 4, an embodiment of the present disclosure provides a device for cleaning an air conditioner, including a processor 100 and a memory 101. Optionally, the device may further include a communication interface 102 and a bus 103. The processor 100, the communication interface 102, and the memory 101 may be communicated with each other through the bus 103. The communication interface 102 may be configured to transmit information. The processor 100 may call logic instructions in the memory 101 to perform the method for cleaning an air conditioner according to the above-mentioned embodiment.

Furthermore, the above-mentioned logic instructions in the memory 101 may be implemented in the form of software functional units and stored in a computer-readable storage medium when sold or used as independent products.

As a computer-readable storage medium, the memory 101 may be configured to store software programs and computer-executable programs, such as program instructions/modules corresponding to the method according to the embodiments of the present disclosure. The processor 100 executes functional applications and data processing, that is, implements the method for cleaning an air conditioner according to the above-mentioned embodiment, by executing the program instructions/modules stored in the memory 101.

The memory 101 may include a program storage region and a data storage region, and the program storage region may store an operating system and an application required for at least one function; the data storage region may store data created according to use of a terminal apparatus, or the like. Furthermore, the memory 101 may include a high speed random access memory and may further include a non-volatile memory.

An embodiment of the present disclosure provides an air conditioner, including the above-mentioned device for cleaning an air conditioner.

An embodiment of the present disclosure provides a computer-readable storage medium storing computer-executable instructions, the computer-executable instructions being configured to perform the above-mentioned method for cleaning an air conditioner.

An embodiment of the present disclosure provides a computer program product, including a computer program stored on a computer-readable storage medium, the computer program including program instructions which, when executed by a computer, cause the computer to perform the above-mentioned method for cleaning an air conditioner.

The above-mentioned computer-readable storage medium may be a transitory computer-readable storage medium or a non-transitory computer-readable storage medium.

The technical solutions of the embodiments of the present disclosure may be implemented in the form of a software product. The computer software product is stored in a storage medium and includes one or more instructions for instructing a computer apparatus (which may be a personal computer, a server, or a network apparatus, or the like) to execute all or a part of steps of the method according to the embodiment of the present disclosure. The aforementioned storage medium may be a non-transitory storage medium, including: any medium that can store program codes, such as a USB flash disk, a removable hard disk, a read-only memory (ROM), a random access memory (RAM), a magnetic disk, or an optical disk, or may be a transient storage medium.

The above description and the drawings sufficiently illustrate the embodiments of the present disclosure to enable those skilled in the art to practice them. Other embodiments may incorporate structural, logical, electrical, process, and other changes. The embodiments merely typify possible variations. Unless expressly required, individual components and functions are optional and the order of operations may vary. Portions and features of some embodiments may be included in or substituted for those of other embodiments. Moreover, the terms used in this application are used to describe the embodiments only and not to limit the claims. As used in the descriptions of the embodiments and the claims, the singular forms "a", "an" and "the" are intended to include the plural forms as well, unless the context clearly indicates otherwise. Similarly, the term "and/or" as used in this application represents containing any and all possible combinations of one or more associated listed items. In addition, the term "comprise" and its variants "comprises" and/or "comprising", etc., when used in this application, specify the presence of stated features, integers, steps, operations, elements, and/or assemblies, but do not preclude the presence or addition of one or more other features, integers, steps, operations, elements, assemblies, and/or groups thereof. With no more restrictions, elements defined by sentence "include one . . . " do not exclude other same elements in the process, method, or apparatus including said elements. Herein, every embodiment may illustrate in emphasis what is different from the other embodiments. The same or similar parts in the embodiments may be references to each other. If methods, products, etc. according to the embodiments correspond to the method sections according to the embodiments, reference may be made to the descriptions of the method sections for relevant parts.

Those skilled in the art may be aware that, in combination with the examples described in the embodiments disclosed in this specification, units and algorithm steps can be implemented by electronic hardware, or a combination of computer software and electronic hardware. Whether the functions are executed by hardware or software may depend on particular applications and design constraint conditions of the technical solutions. Those skilled in the art may use different methods to implement the described functions for each particular application, but it should not be considered that the implementation goes beyond the scope of the embodiments of the present disclosure. It may be clearly understood by those skilled in the art that, for the purpose of convenient and brief description, for a detailed working process of the foregoing system, device, and unit, reference may be made to a corresponding process in the method embodiments, and details are not described herein again.

In the embodiments disclosed herein, the disclosed methods and products (including, but not limited to, devices, apparatuses, or the like) may be implemented in other manners. For example, the described device embodiment is merely exemplary. For example, the unit division may be merely logical function division and may be other division in actual implementation. For example, multiple units or assemblies may be combined or integrated into another system, or some features may be ignored or not performed. In addition, the displayed or discussed mutual couplings or direct couplings or communication connections may be implemented through some interfaces. The indirect couplings or communication connections between the devices or units may be implemented in electronic, mechanical, or other forms. The units described as separate parts may or may not be physically separate, and parts displayed as units may or may not be physical units, may be located in one position, or may be distributed on a plurality of network units. A part or all of the units may be selected according to an actual need to achieve the embodiments. In addition, functional units in the embodiments of the present disclosure may be integrated into one processing unit, or each of the units may exist alone physically, or two or more units are integrated into one unit.

The flowcharts and block diagrams in the drawings illustrate the architecture, functionality, and operation of possible implementations of systems, methods and computer program products according to the embodiments of the present disclosure. In this regard, each block in the flowchart or block diagrams may represent a module, program segment, or portion of code, which includes one or more executable instructions for implementing the specified logical function(s). In some alternative implementations, the functions noted in the block may occur out of the order noted in the figures. For example, two successive blocks may, in fact, be executed substantially concurrently, or the blocks may sometimes be executed in the reverse order, depending upon the functionality involved. In the descriptions corresponding to the flowcharts and block diagrams in the drawings, operations or steps corresponding to different blocks may also occur out of the order disclosed in the description, and sometimes, there is no specific order between different operations or steps. For example, two successive operations or steps may, in fact, be executed substantially concurrently, or the operations or steps may sometimes be executed in the reverse order, depending upon the functionality involved. Each block of the block diagrams and/or flowcharts, and combinations of blocks in the block diagrams and/or flowcharts, can be implemented by special purpose hardware-based systems that perform the specified functions or acts, or combinations of special purpose hardware and computer instructions.

What is claimed is:

1. A method for cleaning an air conditioner, comprising:
in response to a cleaning instruction, controlling frosting on the surface of a target heat exchanger;
after a frosting completion condition is met, controlling defrosting of the frost on the target heat exchanger; and
after a defrosting completion condition is met, reducing the surface temperature of the target heat exchanger to a sterilization temperature and carrying out quick cooling sterilization, wherein a temperature difference between the sterilization temperature and a defrosting temperature during defrosting meets a set temperature change sterilization condition.

2. The method according to claim 1, wherein the set temperature change sterilization condition comprises:

$$T_{defrosting} - T_{sterilization} \geq T_{threshold}$$

wherein $T_{defrosting}$ is the defrosting temperature, $T_{sterilization}$ is the sterilization temperature, and $T_{threshold}$ is not less than 55° C.

3. The method according to claim 1, wherein first quick cooling sterilization parameters of the quick cooling sterilization are obtained according to an outdoor environment temperature; and
the first quick cooling sterilization parameters comprise a first outdoor-fan rotating speed of an outdoor fan and a first frequency of a compressor.

4. The method according to claim 3, wherein the obtaining first quick cooling sterilization parameters of the quick cooling sterilization according to an outdoor environment temperature comprises:
obtaining corresponding quick cooling sterilization parameters from a preset first association relationship according to the outdoor environment temperature, the preset first association relationship comprising a corresponding relationship between the outdoor environment temperature and an outdoor-fan rotating speed and a frequency.

5. The method according to claim 1, wherein a second quick cooling sterilization parameter of the quick cooling sterilization is obtained according to an indoor environment temperature; and
the second quick cooling sterilization parameter comprises a first opening degree of a throttling device.

6. The method according to claim 5, wherein the obtaining a second quick cooling sterilization parameter of the quick cooling sterilization according to an indoor environment temperature comprises:
obtaining a corresponding quick cooling sterilization parameter from a preset second association relationship according to the indoor environment temperature, the preset second association relationship comprising a corresponding relationship between the indoor environment temperature and an opening degree.

7. The method according to claim 1, wherein a first coagulation parameter of the frosting is obtained according to an outdoor environment temperature; and
the first coagulation parameter comprises a second outdoor-fan rotating speed of an outdoor fan.

8. The method according to claim 7, wherein the obtaining a first coagulation parameter of the frosting according to an outdoor environment temperature comprises:
obtaining a corresponding coagulation parameter from a preset third association relationship according to the outdoor environment temperature, the preset third association relationship comprising a corresponding relationship between the outdoor environment temperature and the outdoor-fan rotating speed.

9. The method according to claim 1, wherein second coagulation parameters of the frosting are obtained according to an indoor environment temperature; and
the second coagulation parameters comprise a second frequency of a compressor and a second opening degree of a throttling device.

10. An air conditioner, comprising a processor and a memory storing program instructions, the processor being configured to, when executing the program instructions, perform a method for cleaning an air conditioner;
wherein the method for cleaning an air conditioner comprises:
in response to a cleaning instruction, controlling frosting on the surface of a target heat exchanger;
after a frosting completion condition is met, controlling defrosting of the frost on the target heat exchanger; and
after a defrosting completion condition is met, reducing the surface temperature of the target heat exchanger to a sterilization temperature and carrying out quick cooling sterilization, wherein a temperature difference between the sterilization temperature and a defrosting temperature during defrosting meets a set temperature change sterilization condition.

11. The method according to claim 3, wherein a second quick cooling sterilization parameter of the quick cooling sterilization is obtained according to an indoor environment temperature; and
the second quick cooling sterilization parameter comprises a first opening degree of a throttling device.

12. The method according to claim 4, wherein a second quick cooling sterilization parameter of the quick cooling sterilization is obtained according to an indoor environment temperature; and
the second quick cooling sterilization parameter comprises a first opening degree of a throttling device.

13. The method according to claim 7, wherein second coagulation parameters of the frosting are obtained according to an indoor environment temperature; and
the second coagulation parameters comprise a second frequency of a compressor and a second opening degree of a throttling device.

14. The method according to claim 8, wherein second coagulation parameters of the frosting are obtained according to an indoor environment temperature; and
the second coagulation parameters comprise a second frequency of a compressor and a second opening degree of a throttling device.

15. The air conditioner according to claim 10, wherein in the method for cleaning an air conditioner, first quick cooling sterilization parameters of the quick cooling sterilization are obtained according to an outdoor environment temperature; and
the first quick cooling sterilization parameters comprise a first outdoor-fan rotating speed of an outdoor fan and a first frequency of a compressor.

16. The air conditioner according to claim 15, wherein the obtaining first quick cooling sterilization parameters of the quick cooling sterilization according to an outdoor environment temperature comprises:
obtaining corresponding quick cooling sterilization parameters from a preset first association relationship according to the outdoor environment temperature, the preset first association relationship comprising a corresponding relationship between the outdoor environment temperature and an outdoor-fan rotating speed and a frequency.

17. The air conditioner according to claim 10, wherein in the method for cleaning an air conditioner, a second quick cooling sterilization parameter of the quick cooling sterilization is obtained according to an indoor environment temperature; and
the second quick cooling sterilization parameter comprises a first opening degree of a throttling device.

18. The air conditioner according to claim 17, wherein the obtaining a second quick cooling sterilization parameter of the quick cooling sterilization according to an indoor environment temperature comprises:
obtaining a corresponding quick cooling sterilization parameter from a preset second association relationship according to the indoor environment temperature, the preset second association relationship comprising a corresponding relationship between the indoor environment temperature and an opening degree.

19. The air conditioner according to claim 10, wherein in the method for cleaning an air conditioner, a first coagulation parameter of the frosting is obtained according to an outdoor environment temperature;
the first coagulation parameter comprises a second outdoor-fan rotating speed of an outdoor fan;

the obtaining a first coagulation parameter of the frosting according to an outdoor environment temperature comprises:

obtaining a corresponding coagulation parameter from a preset third association relationship according to the outdoor environment temperature, the preset third association relationship comprising a corresponding relationship between the outdoor environment temperature and the second outdoor-fan rotating speed.

20. The air conditioner according to claim 10, wherein in the method for cleaning an air conditioner, second coagulation parameters of the frosting are obtained according to an indoor environment temperature; and the second coagulation parameters comprise a second frequency of a compressor and a second opening degree of a throttling device.

* * * * *